US012765856B2

(12) United States Patent
Stowasser et al.

(10) Patent No.: US 12,765,856 B2
(45) Date of Patent: Oct. 20, 2026

(54) METHOD FOR X-RAY IMAGING, X-RAY IMAGING SYSTEM, AND COMPUTER PROGRAM PRODUCT

(71) Applicant: Siemens Healthineers AG, Forchheim (DE)

(72) Inventors: Boris Stowasser, Erlangen (DE); Philipp Bernhardt, Forchheim (DE)

(73) Assignee: Siemens Healthineers AG, Forchheim (DE)

( * ) Notice: Subject to any disclaimer, the term of this patent is extended or adjusted under 35 U.S.C. 154(b) by 141 days.

(21) Appl. No.: 18/924,092

(22) Filed: Oct. 23, 2024

(65) Prior Publication Data

US 2025/0143659 A1 May 8, 2025

(30) Foreign Application Priority Data

Nov. 2, 2023 (DE) ..................... 10 2023 210 870.4

(51) Int. Cl.
*A61B 6/00* (2024.01)
*G06T 5/50* (2006.01)

(52) U.S. Cl.
CPC ............ *A61B 6/5241* (2013.01); *A61B 6/481* (2013.01); *A61B 6/5258* (2013.01); *G06T 5/50* (2013.01); *G06T 2207/20221* (2013.01); *G06T 2207/20224* (2013.01)

(58) Field of Classification Search
CPC ........... G06T 5/50; G06T 5/70; A61B 6/5241; A61B 6/481; A61B 6/5258; G16H 30/20; G06V 10/30
See application file for complete search history.

(56) References Cited

U.S. PATENT DOCUMENTS

2017/0154413 A1 6/2017 Yu
2018/0336666 A1* 11/2018 Kim .......................... G06T 5/00
2019/0035058 A1 1/2019 Strobel et al.
2021/0142889 A1 5/2021 Stowasser
2023/0037260 A1* 2/2023 Manhart ................ A61B 6/504
(Continued)

FOREIGN PATENT DOCUMENTS

DE 102019217220 A1 5/2021
DE 102021208272 A1 2/2023

OTHER PUBLICATIONS

Elad, Michael, and Michal Aharon. "Image denoising via sparse and redundant representations over learned dictionaries." IEEE Transactions on Image processing 15.12 (2006): 3736-3745.
(Continued)

*Primary Examiner* — Casey Bryant
(74) *Attorney, Agent, or Firm* — Lempia Summerfield Katz LLC

(57) ABSTRACT

In an X-ray imaging procedure, an input image and an input mask image are generated on the basis of first and second detector data of an X-ray flat panel detector. By applying noise suppression, a mask signal image and a signal image are generated on the basis thereof. By calculating the difference between the signal image and the mask signal image, a subtraction image is generated. The subtraction image is scaled so that a number of pixels is increased in a first image direction. A results image is generated in which the scaled subtraction image and a noise image are added together.

18 Claims, 3 Drawing Sheets

(56) References Cited

U.S. PATENT DOCUMENTS

| | | | | |
|---|---|---|---|---|
| 2023/0065392 | A1* | 3/2023 | Djelouah | G06T 5/70 |
| 2024/0311980 | A1 | 9/2024 | Stowasser | |

OTHER PUBLICATIONS

Islam, Sheikh Md Rabiul, Xu Huang, and Dharmendra Sharma. "Wavelet based denoising algorithm of the ECG signal corrupted by WGN and Poisson noise." 2012 International Symposium on Communications and Information Technologies (ISCIT). IEEE, 2012. pp. 165-168.

Lehtinen, Jaakko, et al. "Noise2noise: Learning image restoration without clean data (2018)." arXiv preprint arXiv:1803.04189. pp. 1-12.

* cited by examiner

METHOD FOR X-RAY IMAGING, X-RAY IMAGING SYSTEM, AND COMPUTER PROGRAM PRODUCT

The present patent document claims the benefit of German Patent Application No. 10 2023 210 870.4, filed Nov. 2, 2023, which is hereby incorporated by reference in its entirety.

TECHNICAL FIELD

The present disclosure relates to a method for X-ray imaging, wherein detector data is received from an X-ray flat panel detector. The disclosure further relates to a data processing device for performing such a method, an X-ray imaging system with such a data processing device and an X-ray flat panel detector, as well as corresponding computer program products.

BACKGROUND

In various techniques for X-ray-based imaging, a mask image is subtracted from another X-ray image, (also referred to as a live image or an input image), of the same mapped area, in order to emphasize differences between the mask image and the live image and to mask out (subtract out) irrelevant parts of the X-ray image, (e.g., anatomical background). Examples of this are methods for digital subtraction angiography (DSA) or roadmap methods. Depending on the variant, the mask image may be acquired without the administration of contrast agent and/or without a tool, whereas a contrast agent and/or the tool are present when the live image is acquired. In the resulting subtraction image, a vascular structure highlighted by the contrast agent and/or the tool is visible, whereas interfering or irrelevant parts of the image, (e.g., the image background), which are also present in the mask image, are not shown in the subtraction image.

To acquire the mask image and the live image, X-ray flat panel detectors may be used, which have, arranged in a detector array, a plurality of individual detectors or detector pixels along a first image direction and a second image direction perpendicular thereto. In various applications, so-called zoom stages are used in which in each case only a partial area, (e.g., a rectangular partial area), of the entire X-ray flat panel detector is used to generate the overall image. The subtraction image is scaled up to the target resolution of the display device for display on a display device that has a higher resolution in terms of a higher number of pixels than the partial area used of the detector array in at least one of the image directions, (e.g., in both image directions). In other words, a digital zoom is performed. Known interpolation methods are employed here.

The interpolation methods employed may be based on bilinear or bicubic interpolation, edge-adaptive interpolation, super-resolution approaches, and/or the use of artificial neural networks.

One disadvantage of this is that in X-ray imaging the lowest possible X-ray doses are used, which leads to a comparatively high noise component. Due to the upscaling and interpolation of the subtraction image to the target resolution, there is firstly a reduced image sharpness, particularly in the signal component of the subtraction image, but secondly also a changed visual representation of the noise component.

One possibility for improving the resulting image quality would be to apply noise suppression algorithms to the subtraction image in order to reduce the noise component. However, since known noise suppression algorithms do not work entirely accurately, this may result in artifacts that may distract the user and impede or distort the interpretation of the displayed image.

With regard to the noise component, the visual representation of the upscaled noise component is different in different zoom stages. This leads to different image impressions at different zoom stages, which may likewise impede or distort the interpretation of the displayed image.

The publication S. M. Rabiul Islam et al., "Wavelet based denoising algorithm of the ECG signal corrupted by WGN and Poisson noise," 2012 International Symposium on Communications and Information Technologies (ISCIT), Gold Coast, QLD, Australia, 2012, pp. 165-168, describes a noise suppression algorithm based on a wavelet transformation. The publication M. Elad et al., "Image Denoising Via Sparse and Redundant Representations Over Learned Dictionaries," IEEE Transactions on Image Processing, vol. 15, no. 12, pp. 3736-3745 Dec. 2006, describes a noise suppression algorithm based on the non-local means approach. The publication J. Lehtinen et al., "Noise2Noise: Learning Image Restoration without Clean Data", arXiv: 1803.04189, describes a method for noise suppression in images, which is based on the use of artificial noise. Furthermore, noise suppression algorithms exist that are based on the principle of singular spectrum analysis. This method uses singular spectrum analysis to split a signal into its components. The noise in the components may then be identified and removed. Further noise suppression algorithms are based on convolutional neural networks (CNNs). In this case, CNNs are trained to remove noise from images or signals.

Known from the publication DE 10 2019 217 220 A1 is a method for providing an output dataset as a function of an input dataset, wherein the method includes: determination of a noise-reduced signal dataset from the input dataset; determination of a noise dataset as the difference between the input dataset and the signal dataset; determination of a modified noise dataset from the noise dataset and/or determination of a modified signal dataset from the signal dataset; and determination of an output dataset by addition of the modified noise dataset to the signal dataset or to the modified signal dataset or by addition of the noise dataset to the modified signal dataset.

Known from the publication DE 10 2021 208 272 A1 is a method for reducing noise and movement artifacts when generating a subtraction image. Multiple mask images of an object are obtained prior to the administration of a contrast agent. A mapping of the object is obtained after the administration of the contrast agent. A first summation image is obtained by weighted summation of the mask images, wherein the individual weights of the mask images are automatically determined by an optimization method. The subtraction image is determined by subtraction of the summation image from the mapping.

Known from the publication US 2019/0035058 A1 is a method for processing an X-ray image, which includes a variance stabilization transformation. In this case, a transformation parameter of the variance stabilization transformation is dependent on a property of the X-ray image, which in turn depends on the X-ray imaging device and/or an acquisition parameter of the X-ray image. Noise-reduced data is generated from the variance-stabilized data, and by an inverse variance stabilization transformation a denoised X-ray image is generated therefrom.

Known from the publication US 2017/0154413 A1 is a method for denoising of a dynamic image. The dynamic image may represent a time series of snapshot images. With the help of a "sparsifying transformation," the dynamic image is transformed into an aggregated image and a series of transformation domain images. The transformation domain images represent kinetic information of the dynamic images, (e.g., differences between the snapshots), and the aggregated image represents static information, (e.g., features and structures that are common to the snapshots). The transformation domain images are denoised. The denoised transformation domain images are recombined with the aggregated image using an inverse "sparsifying transformation" in order to generate a denoised dynamic image.

SUMMARY AND DESCRIPTION

It is an object of the present disclosure to overcome, at least in part, the disadvantages mentioned resulting from the upscaling of the noise component. The scope of the present disclosure is defined solely by the appended claims and is not affected to any degree by the statements within this summary. The present embodiments may obviate one or more of the drawbacks or limitations in the related art.

The disclosure relates to using noise suppression in both the mask image and the input image to reduce the noise before generating the subtraction image, generating the subtraction image, scaling the subtraction image using interpolation, and then deliberately adding noise back to the scaled subtraction image.

In accordance with one aspect, a method for X-ray imaging is specified. In this case, first detector data is received from an X-ray flat panel detector and, on the basis of the first detector data, an input mask image is generated, which represents a region to be mapped of an object in a first state. Second detector data is received from the X-ray flat panel detector and, on the basis of the second detector, data an input image is generated, which represents the region to be mapped of the object in a second state. By applying noise suppression, in particular a noise suppression algorithm, to the input mask image, a mask signal image is generated. By applying noise suppression, in particular the noise suppression algorithm or a further noise suppression algorithm, to the input image, a signal image is generated. By calculating the difference between the signal image and the mask signal image, or between the signal image and an image dependent on the mask signal image, or between an image dependent on the signal image and the mask signal image, or between the image dependent on the signal image and the image dependent on the mask signal image, a subtraction image is generated.

A scaled subtraction image is generated in that the subtraction image is scaled, in particular upscaled, by applying an interpolation method, so that at least in a first image direction a number of pixels of the scaled subtraction image is greater than a number of pixels of the subtraction image. A results image is generated in that the scaled subtraction image and a noise image are added together.

The method may be purely computer-implemented. Unless specified otherwise, all acts of the computer-implemented method may be performed by a data processing device, which has at least one computing unit. In particular, the at least one computing unit is configured or adapted for the performance of the acts of the computer-implemented method. To this end, the at least one computing unit may store a computer program containing commands which when executed by the at least one computing unit cause the at least one computing unit to execute the computer-implemented method.

For each embodiment of the computer-implemented method, corresponding embodiments of the method emerge that are not purely computer-implemented, in that corresponding method acts are also included, according to which the first detector data and/or the second detector data is generated by the X-ray flat panel detector.

Unless not otherwise explicitly mentioned below, an image refers to an image in the spatial domain.

The input mask image and the input image in particular have the same number of pixels and the same aspect ratio. Accordingly, for example, the subtraction image likewise has, before it is scaled, the same number of pixels as the input mask image and the input image.

The results image or an image dependent on the results image may be displayed on a display screen.

The input image and the input mask image are in particular X-ray projection images. To generate the respective detector data, X-ray radiation is emitted, thus in particular by an X-ray source, in the direction of the region to be mapped of the object and the detector data is generated by the X-ray flat panel detector on the basis of portions of the X-ray radiation passing through the object.

The first state is present during a first period, during which the first detector data is generated, and the second state is present during a second period, during which the second detector data is generated. The second period in particular lies after the first period.

The first state and the second state may differ by the presence of a contrast agent in the region to be mapped, which in particular contains one or more blood vessels. The first state may correspond to a state in which no contrast agent is present in the region to be mapped and the second state may correspond to a state in which contrast agent is present in the region to be mapped. The contrast agent may be administered between the first period and the second period. The subtraction image then only shows the region in which the contrast agent is present, in other words the one or more blood vessels, or the region in which the contrast agent is present is highlighted particularly strongly in the subtraction image and is accordingly readily identifiable.

The first state and the second state may differ, additionally or alternatively, by the presence of a tool in the region to be mapped. The first state for may correspond to a state in which the tool is not present in the region to be mapped or in a defined subregion thereof, and the second state may correspond to a state in which the tool is present in the region to be mapped or in the subregion thereof. The tool may be introduced between the first period and the second period. The subtraction image then only shows the tool, or the tool is highlighted particularly strongly in the subtraction image and is accordingly readily identifiable. At least one further image may also be superimposed on the results image when displayed on the display device, for instance an image that only shows vessels into which the tool is introduced or highlights these. The tool may be a vascular catheter and/or a vascular prothesis or a stent or a guide wire or similar.

The first detector data may correspond to an acquisition interval, also called a frame, so that exactly one X-ray projection image, namely the input mask image, results from the first detector data. However, it is also possible for the first detector data to correspond to multiple frames. In this case, multiple X-ray projection images may be generated on the basis of the first detector data, one for each frame. The input mask image may then correspond to one of the X-ray projection images or may be generated by averaging or weighted averaging of the X-ray projection images.

It is also possible that when selecting the X-ray projection image or the weighted averaging a degree of similarity between the X-ray projection image and the input image is calculated in each case and one of the X-ray projection images dependent on the degrees of similarity is selected as the input mask image or corresponding weighting factors for the weighted averaging dependent on the degrees of similarity are calculated. In this way, it is possible to provide that the contents of the input image that are also present in the input mask image, and in particular may be removed during the generation of the subtraction image, correspond as closely as possible to those of the input mask image. The degree of similarity may be calculated as an L2 distance or more complex measures may be used, for example, also using segmentations, etc. The second detector data may also correspond to one or more frames and consequently to one or more X-ray projection images. The input image may be selected from the X-ray projection images.

The noise suppression algorithm or the further noise suppression algorithm may be known noise suppression algorithms. They may be performed in accordance with the publications concerning noise suppression algorithms cited in the introduction. The interpolation method may likewise be performed on the basis of one of the interpolation methods cited in the introduction.

The noise suppression results in the noise component in the signal image being less than in the input image, (e.g., no longer being present), and in the noise component in the mask signal image being less than in the input mask image, (e.g., no longer being present). For example, a signal-to-noise ratio of the signal image is greater than a signal-to-noise ratio of the input image and a signal-to-noise ratio of the mask signal image is greater than a signal-to-noise ratio of the input mask image.

In conventional approaches, in which the noise suppression is not performed before generating and scaling the subtraction image, the visual representation of the upscaled noise component depends on the respective zoom stage. This dependency is thereby avoided in accordance with the disclosure. The noise image may be generated such that it results in the same or substantially the same visual representation for all zoom stages. Even if in conventional methods a noise suppression were to be performed after the generation and prior to the scaling of the subtraction image or after the scaling of the subtraction image, this would potentially result in undesirable artifacts. This is also avoided in accordance with the disclosure.

In addition, it has been shown, against expectations, that when the noise image is added to the scaled subtraction image, the visual impression when displaying the results image is improved, in the sense that a trained observer may better perceive anatomical structures and/or other contents represented in the results image. Furthermore, as a result, the independence of the visual impression when displaying the results image is improved by the zoom stage.

The noise image is in particular generated in that the respective number of pixels in the first and the second image direction of the noise image is the same as the respective number of pixels in the first and second image direction of the scaled signal image. The individual pixel values may hence be added together to generate the results image.

In certain embodiments, the noise image may be generated independently of the first detector data and/or the second detector data. For example, white noise may be used to generate the noise image. However, it is also possible for the noise image to be generated independently of the first detector data and/or the second detector data. This has the advantage that the noise characteristic of the X-ray flat panel detector is in any case retained.

In accordance with at least one embodiment, an initial noise image is generated by calculating the difference between the input image and the signal image. The noise image is generated in that a spatial frequency spectrum of the initial noise image or of an image dependent on the initial noise image is expanded so that a maximum spatial noise frequency corresponding to the first image direction is increased.

Due to the noise suppression and the calculation of the difference, in other words, the subtraction of the input image from the signal image or vice versa, the input image is thus split into the signal image and the initial noise image. In certain examples, the signal image does not contain any noise components, whereas the initial noise image would contain exclusively noise components and in particular all noise components of the input image. However, depending on input image and noise suppression algorithm used, this case may not occur. Nonetheless, the noise components dominate in the initial noise image, whereas in the signal image the noise components play a subsidiary role.

The initial noise image is a discrete digital image. The frequency spectrum of the initial noise image may be calculated by a discrete Fourier transform, (e.g., a fast Fourier transform (FTT) or similar). Since the initial noise image is a two-dimensional image, the frequency spectrum is likewise a two-dimensional frequency spectrum. In certain embodiments, the frequency spectrum is expanded in accordance with the first image direction. Alternatively, the frequency spectrum may be expanded both in accordance with the first and in accordance with the second image direction, so that the respective maximum noise frequency is increased in both image directions.

The expansion of the frequency spectrum may be done in various ways. For example, the expansion may be performed in the frequency space. To this end, the frequency spectrum of the initial noise image is calculated, in particular by the aforementioned discrete Fourier transform. Because of the discrete nature of the initial noise image, a maximum spatial noise frequency of the frequency spectrum corresponding to the first image direction exists and a further maximum noise frequency corresponding to the second image direction. The maximum noise frequency is in this case given by the inverse pixel size of the initial noise image in the first image direction and the further maximum noise frequency by the inverse pixel size of the initial noise image in the second image direction.

If the initial noise image were to be upscaled in the conventional manner so that the number of pixels and pixel size of the upscaled initial noise image corresponded to the scaled subtraction image, the corresponding amplitudes of the frequency components would be equal to zero in the scaled initial noise image at high frequencies. This would result in an inconsistent noise impression or an inconsistent representation of the noise component, if the thus scaled initial noise image were added together with the scaled subtraction image and displayed. Hence, in certain embodiments, the frequency spectrum is expanded such that the maximum noise frequency of the initial noise image is in any case increased along the first image direction.

Where appropriate, corresponding normalizations are also performed in order to adjust the pixel size and number of pixels of the noise image to those of the scaled subtraction image.

The fact that the frequency spectrum of the initial noise image is expanded may be understood to mean that the frequency spectrum in particular corresponding to the first image direction is supplemented with frequency components, so that the maximum spatial noise frequency is correspondingly increased. For example, the supplemented frequency components may be determined on the basis of white noise. For example, the initial noise image may also be scaled analogously to the subtraction image and a modulation transfer function (MTF) may be calculated as follows as a function of the frequencies f1, f2 corresponding to the first or second image direction:

$$MTF\ (f1, f2) = 1 - \frac{A'(f1, f2)}{A(f1, f2)},$$

where A (f1,f2) represents the corresponding amplitude in the frequency space prior to scaling and A' (f1,f2) the corresponding amplitude in the frequency space after scaling.

The MTF may be convoluted with a white noise spectrum and the result added to A' (f1,f2). If the sum is transformed back by inverse Fourier transform into the spatial domain, the noise image is for example obtained.

However, in other embodiments, the frequency spectrum may also be expanded directly in the spatial domain. To this end, the initial noise image may be scaled analogously to the subtraction image and amplitude values may be statistically inserted at those resulting pixels where no amplitude values are present in the spatial domain in the scaled initial noise image in accordance with a specified variance. The variance may in this case correspond to a variance of the original initial noise image.

In a multi-scalar approach, the initial noise image may also be split into multiple frequency bands, in that the principle of Laplacian pyramids may be applied. The resulting frequency-band-specific initial noise images are then scaled like the scaled subtraction image. For each frequency-band-specific initial noise image, a variance may be calculated and the unfilled pixels in the frequency-band-specific scaled initial noise images corresponding to the thus determined variances may be filled with statically distributed amplitude values. The noise image may then be generated in that the supplemented frequency-band-specific scaled initial noise images are reassembled, in particular in accordance with the principle of Laplacian pyramids.

This is particularly advantageous if the noise in the initial noise image is colored, for example, due to the MTF of the X-ray flat panel detector. Because in the case of Poisson noise the variance is amplitude-dependent, it is particularly advantageous here to apply a variance-stabilizing transformation in advance, as described below for certain embodiments. If the Poisson noise is superimposed by electrical noise, not only the variance but also the color is a function of the level. A variance- and covariance-stabilizing transformation would then be even more advantageous.

Thus, in certain embodiments, the same noise characteristic in the resulting results image may be achieved for different sizes of the input image and of the input mask image thanks to a corresponding expansion of the frequency spectrum to the same maximum noise frequency. A user may draw no conclusions from the results image regarding the size of the input image or of the input mask image and of the accordingly applied portion or section of the detector array of the X-ray flat panel detector. In other words, the visual representation of the noise component in the results image does not differ for different sizes of the input image or of the input mask image. This is advantageous in particular since a consistent noise impression is important for the reliable interpretation of the results image.

The above explanations relate to the expansion of the spatial frequency spectrum of the initial noise image. In such embodiments, the noise image in particular is generated independently of the first detector data or the input mask image. This may be useful in particular if a significantly higher X-ray dose per frame is employed for generating the first detector data than for generating the second detector data. In this case, the noise component in the input mask image is namely for example significantly less than in the input image and may where appropriate be disregarded.

However, the noise image may also be generated dependent on the input image and dependent on the input mask image. For example, the image dependent on the initial noise image may be dependent on the initial noise image and the input mask image. The above explanations may be transferred analogously to embodiments in which it is not the spatial frequency spectrum of the initial noise image that is expanded, but instead the spatial frequency spectrum of the image dependent on the initial noise image is expanded.

According to at least one embodiment, by calculating the difference between the input mask image and the mask signal image, a mask noise image is generated. The image dependent on the initial noise image is generated by addition or weighted addition of the initial noise image and the mask noise image. The noise image is generated in that the spatial frequency spectrum of the image dependent on the initial noise image is expanded so that the maximum spatial noise frequency corresponding to the first image direction is increased.

As a result, the consistency of the noise characteristic in the results image is further increased.

According to at least one embodiment, a first raw image is generated on the basis of the first detector data by the at least one computing unit and the input mask image is generated by applying a variance-stabilizing transformation, in particular an Anscombe transformation, to the first raw image.

According to at least one embodiment, a second raw image is generated on the basis of the second detector data by the at least one computing unit and the input image is generated by applying a variance-stabilizing transformation, in particular an Anscombe transformation, to the second raw image.

Due to the variance-stabilizing transformation, the variance of the noise in the input mask image or in the input image is at least approximately independent of the level, i.e., the local mean value of the noise. In the raw images, the variance of the noise is, for example, proportional to the mean value, since the noise follows a Poisson distribution.

Due to the variance-stabilizing transformation, it is therefore ultimately possible to provide that the distribution of the noise component in the results image is independent of the brightness of the parts of the image represented.

In certain embodiments, the variance-stabilizing transformation is a variance- and covariance-stabilizing transformation.

As a result, as mentioned above, the dependence of the color of the noise on the level of the noise is compensated for.

According to at least one embodiment, the image dependent on the signal image is generated in that at least one image processing act is performed.

According to at least one embodiment, the at least one image processing act includes an inverse variance-stabilizing transformation, in particular the inverse transformation to the variance-stabilizing transformation that is applied to the second raw image in order to generate the input image.

In this way, the effects of the variance-stabilizing transformation are only felt during the processing of the initial noise image, but not during the processing of the signal image. In this way artifacts that otherwise occur in the signal path are prevented.

According to at least one embodiment, the at least one image processing act includes at least one grayscale transformation.

In this way, the contrasts in the signal path may be improved. The grayscale transformation may contain a logarithmic grayscale transformation. Thus, a logarithm of the corresponding pixel values is formed in the signal path, in order, in accordance with the exponential nature of the law of attenuation for the attenuation of the X-ray radiation, to achieve a homogeneous brightness distribution in the results image.

According to at least one embodiment, the at least one image processing act includes the application of at least one frequency filter, for example, at least one bandpass filter and/or at least one multi-scalar filter.

According to at least one embodiment, the image dependent on the mask signal image is generated in that at least one further image processing act is performed.

According to at least one embodiment, the at least one further image processing act includes an inverse variance-stabilizing transformation, in particular the inverse transformation to the variance-stabilizing transformation that is applied to the first raw image in order to generate the input mask image.

In this way, the effects of the variance-stabilizing transformation are only felt during the processing of the mask noise image, but not during the processing of the mask signal image. In this way artifacts that otherwise occur in the signal path are prevented.

According to at least one embodiment, the at least one further image processing act includes at least one further grayscale transformation.

In this way, the contrasts in the signal path may be improved. The further grayscale transformation may include a logarithmic grayscale transformation.

According to at least one embodiment, the at least one further image processing act includes the application of at least one frequency filter, for example, at least one bandpass filter and/or at least one multi-scalar filter.

According to at least one embodiment, the number of pixels of the scaled subtraction image in the first image direction corresponds to a number of pixels of the display screen in the first image direction.

According to at least one embodiment, the increased maximum spatial noise frequency corresponds to an inverse pixel size of the display screen in the first image direction.

According to at least one embodiment, the first detector data includes respective pixel values for detector pixels of a specified section of the detector array of the X-ray flat panel detector, in particular all detector pixels of the specified section and only the detector pixels of the specified section.

The input mask image is thus an input mask image corresponding to a specified zoom stage that corresponds to the specified section.

According to at least one embodiment, the second detector data includes respective pixel values for detector pixels of the specified section of the detector array of the X-ray flat panel detector, in particular all detector pixels of the specified section and only the detector pixels of the specified section.

The input image is thus an input image corresponding to the specified zoom stage that corresponds to the specified section.

According to at least one embodiment, the subtraction image is scaled by applying the interpolation method, so that in the second image direction, which in particular is perpendicular to the first image direction, a number of pixels of the scaled subtraction image is greater than a number of pixels of the subtraction image.

According to at least one embodiment, to generate the noise image the spatial frequency spectrum of the initial noise image or of the image dependent on the initial noise image is expanded such that a further maximum spatial noise frequency corresponding to the second image direction is increased.

The above explanations regarding the increase in the maximum spatial noise frequency corresponding to the first image direction may be transferred analogously to the increase in the further maximum spatial noise frequency corresponding to the second image direction.

According to at least one embodiment, X-ray radiation is emitted in the direction of the region to be mapped of the object by an X-ray source, while the object is in the first state, and the first detector data is generated by the X-ray flat panel detector on the basis of portions of the X-ray radiation passing through the region to be mapped of the object. Further X-ray radiation is emitted in the direction of the region to be mapped of the object by the X-ray source, while the object is in the second state, and the second detector data is generated by the X-ray flat panel detector on the basis of portions of the further X-ray radiation passing through the region to be mapped of the object.

According to a further aspect, a data processing device having at least one computing unit is specified. The at least one computing unit is configured to perform a method for X-ray imaging, e.g., a computer-implemented method.

A computing unit may be understood as a data processing device that contains a processing circuit. The computing unit may process data for the performance of computing operations. Where appropriate, this also includes operations in order to perform indexed accesses to a data structure, for example a look-up table (LUT).

The computing unit may contain one or more computers, one or more microcontrollers, and/or one or more integrated circuits, for example, one or more application-specific integrated circuits (ASIC), one or more field-programmable gate arrays (FPGA), and/or one or more systems on a chip (SoC). The computing unit may also contain one or more processors, for example, one or more microprocessors, one or more central processing units (CPU), one or more graphics processing units (GPU) and/or one or more signal processors, in particular one or more digital signal processors (DSP). The computing unit may also contain a physical or a virtual group of computers or other of the aforementioned units.

In various embodiments, the computing unit contains one or more hardware and/or software interfaces and/or one or more storage units.

A storage unit may be designed as a volatile data memory, for example, as a dynamic random access memory (DRAM) or a static random access memory (SRAM), or as a non-volatile data memory, for example, as a read-only memory (ROM), as a programmable read-only memory (PROM), as an erasable programmable read-only memory (EPROM), as an electrically erasable programmable read-only memory (EEPROM), as a flash memory or flash EEPROM, as a ferroelectric random access memory (FRAM), as a magnetoresistive random access memory (MRAM), or as a phase-change random access memory (PCRAM).

According to a further aspect, an X-ray imaging system is specified that has an X-ray source and an X-ray flat panel detector. The X-ray imaging system has a data processing device, wherein the at least one computing unit is designed to perform a method for X-ray imaging and to this end to actuate the X-ray source to generate the X-ray radiation and the further X-ray radiation and to receive the first detector data and the second detector data from the X-ray detector.

According to at least one embodiment, the X-ray imaging system has a display screen and the at least one computing unit is configured to display the results image or an image dependent on the results image on the display screen.

Further embodiments of the X-ray imaging system follow directly from the various embodiments of the method and vice versa. In particular, individual features and corresponding explanations and advantages regarding the various embodiments may be transferred to the method analogously to corresponding embodiments of the X-ray imaging system. In particular, the X-ray imaging system is designed or programmed to perform a method. In particular, the X-ray imaging system performs the method.

According to a further aspect, a first computer program is specified that has the first commands. If the first commands are executed by a data processing device, in particular a data processing device, the first commands cause the data processing device to execute a method for X-ray imaging, e.g., a computer-implemented method.

The first commands may be present as program code. The program code may be provided as binary code or assembler and/or as source code of a programming language, (e.g., C), and/or as a program script, (e.g., Python).

According to a further aspect, a second computer program containing second commands is specified. If the second commands are executed by an X-ray imaging system, in particular by the data processing device of the X-ray imaging system, the second commands cause the X-ray imaging system to perform a method for X-ray imaging.

The second commands may be present as program code. The program code may be provided as binary code or assembler and/or as source code of a programming language, (e.g., C), and/or as a program script, (e.g., Python).

According to a further aspect, a computer-readable storage medium is specified, which stores a first computer program in accordance with the disclosure and/or a second computer program in accordance with the disclosure.

The first computer program, the second computer program, and the computer-readable storage medium may be referred to as respective computer program products having the first or the second commands.

Further features and combinations of features of the disclosure emerge from the figures and the description thereof, and from the claims. In particular, further embodiments of the disclosure need not necessarily contain all the features of one of the claims. Further embodiments of the disclosure may have features or combinations of features that are not mentioned in the claims.

The disclosure is explained in greater detail below on the basis of specific embodiments and associated schematic drawings. In the figures, identical or functionally identical elements may be provided with the same reference characters. The description of identical or functionally identical elements is where appropriate not necessarily repeated in respect of different figures.

DETAILED DESCRIPTION

Figure 1:
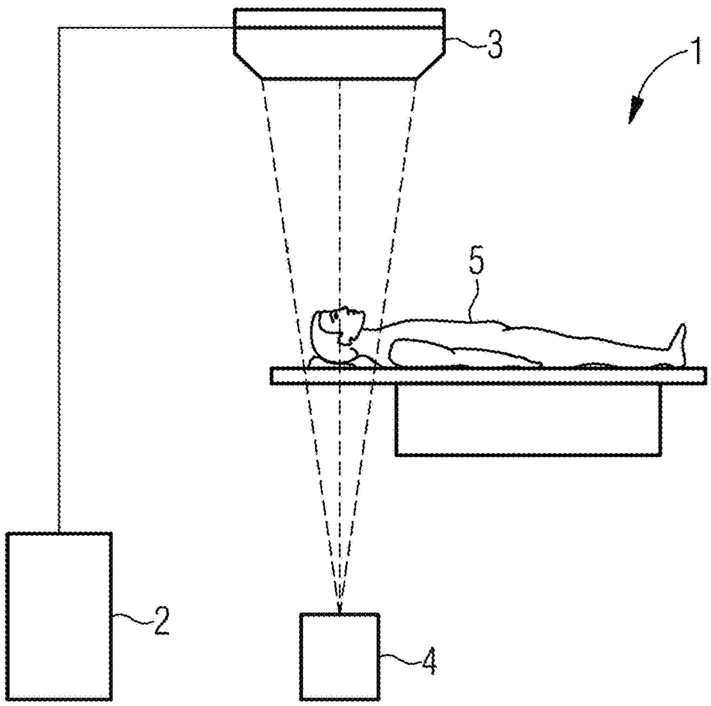
FIG. 1 depicts a schematic representation of an embodiment of an X-ray imaging system.

FIG. 1 schematically shows an embodiment of an X-ray imaging system 1 with an X-ray source 4, an X-ray flat panel detector 3, and at least one computing unit, which for the sake of simplicity is shown in FIG. 1 as a single computing unit 2. An object 5, in particular a part of a patient's body, may be placed in a beam path of the X-ray radiation that may be emitted by the X-ray source 4. Portions of the X-ray radiation passing through the object 5 hit a detector array of the X-ray flat panel detector 3 and this generates detector data on the basis of the detected portions of the X-ray radiation, in particular using a specified section of the detector array and makes this available to the computing unit 2.

The computing unit 2 may generate a results image 15 (see FIG. 2) by performing a method for X-ray imaging and may actuate a display screen (not shown) of the X-ray imaging system 1 to display the results image 15 or an image dependent thereon.

Figure 2:
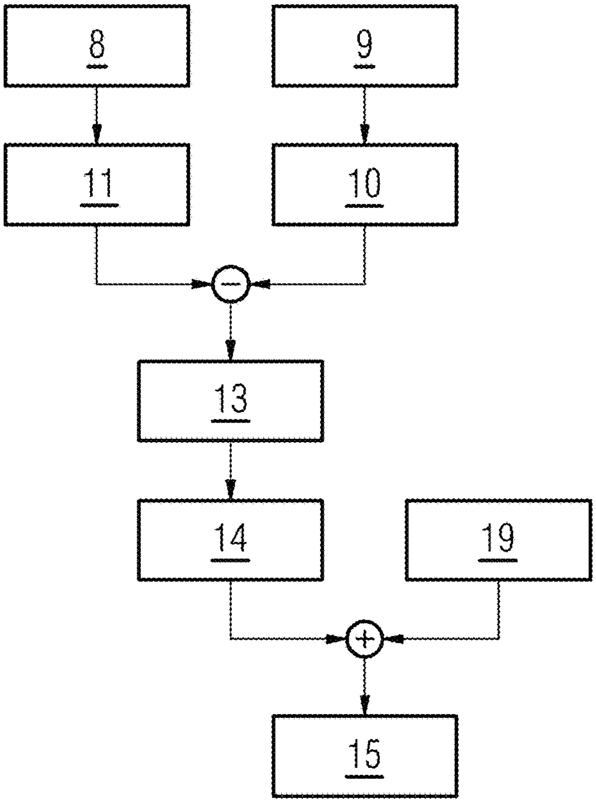
FIG. 2 depicts a schematic flow diagram of an embodiment of a method for X-ray imaging.

FIG. 2 schematically shows a schematic flow diagram of an embodiment of a method for X-ray imaging.

The computing unit 2 in this case receives first detector data from the X-ray flat panel detector 3 and, on the basis of the first detector data, generates an input mask image 8, which represents a region to be mapped of the object 5, (e.g., a vascular tree), in a first state, (e.g., without contrast agent). The computing unit 2 receives, in particular thereafter, (e.g., after administration of a contrast agent), second detector data from the X-ray flat panel detector 3 and, on the basis of the second detector data, generates an input image 9, also referred to as a live image, which shows the region to be mapped of the object 5 in a second state, (e.g., with the contrast agent).

By applying noise suppression to the input mask image 8, the computing unit 2 generates a mask signal image 11. Further, by applying noise suppression to the input image 9, the computing unit 2 generates a signal image 10.

By calculating the difference between the signal image 10 and the mask signal image 10, or in each case images dependent thereon, the computing unit 2 generates a subtraction image 13. The computing unit 2 generates a scaled subtraction image 14 in that the subtraction image 13 is scaled by applying an interpolation method, so that in a first image direction a number of pixels of the scaled subtraction image 14 is greater than a number of pixels of the subtraction image 13. The computing unit 2 generates the results image 15 in that the scaled subtraction image 14 and a noise image 19 are added together. The noise image 19 may be an artificial noise image based on white noise.

Figure 3:
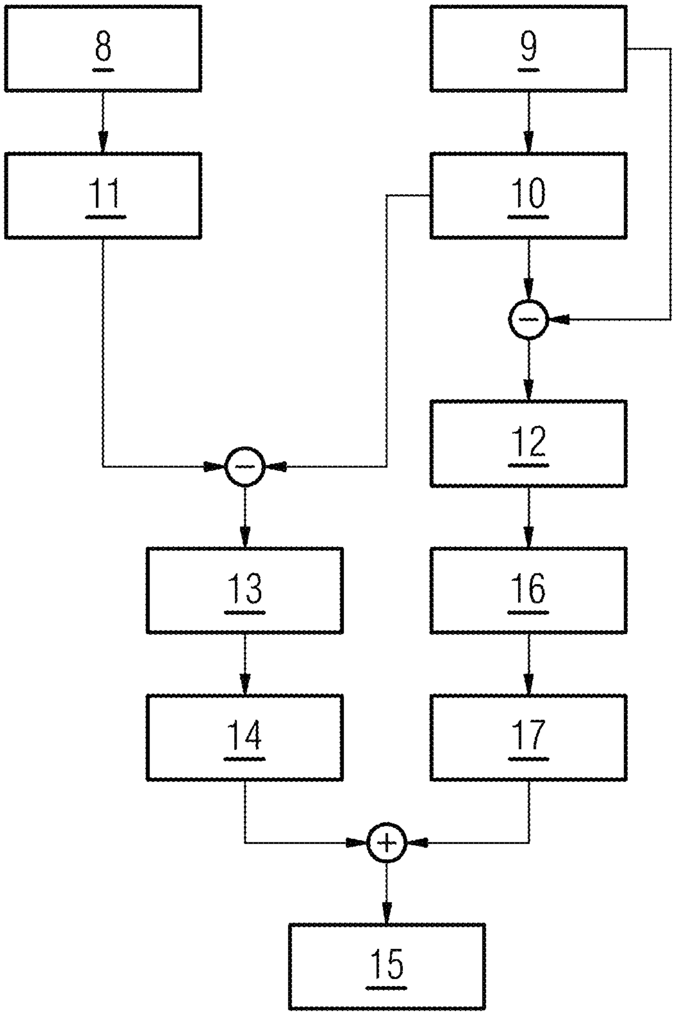
FIG. 3 depicts a schematic flow diagram of a further embodiment of a method for X-ray imaging.

FIG. 3 shows a schematic flow diagram of an embodiment of a method for X-ray imaging, which is based on the embodiment described in respect of FIG. 2.

Instead of the noise image 19, a noise image 17, which depends on the input image 9, is here added to the scaled signal image 14. By calculating the difference between the input image 9 and the signal image 10, an initial noise image 12 is generated. The noise image 17 is generated in that a spatial frequency spectrum 6 (see FIG. 5) of the initial noise image 12 is expanded so that a maximum spatial noise frequency corresponding to the first image direction is increased.

Figure 4:
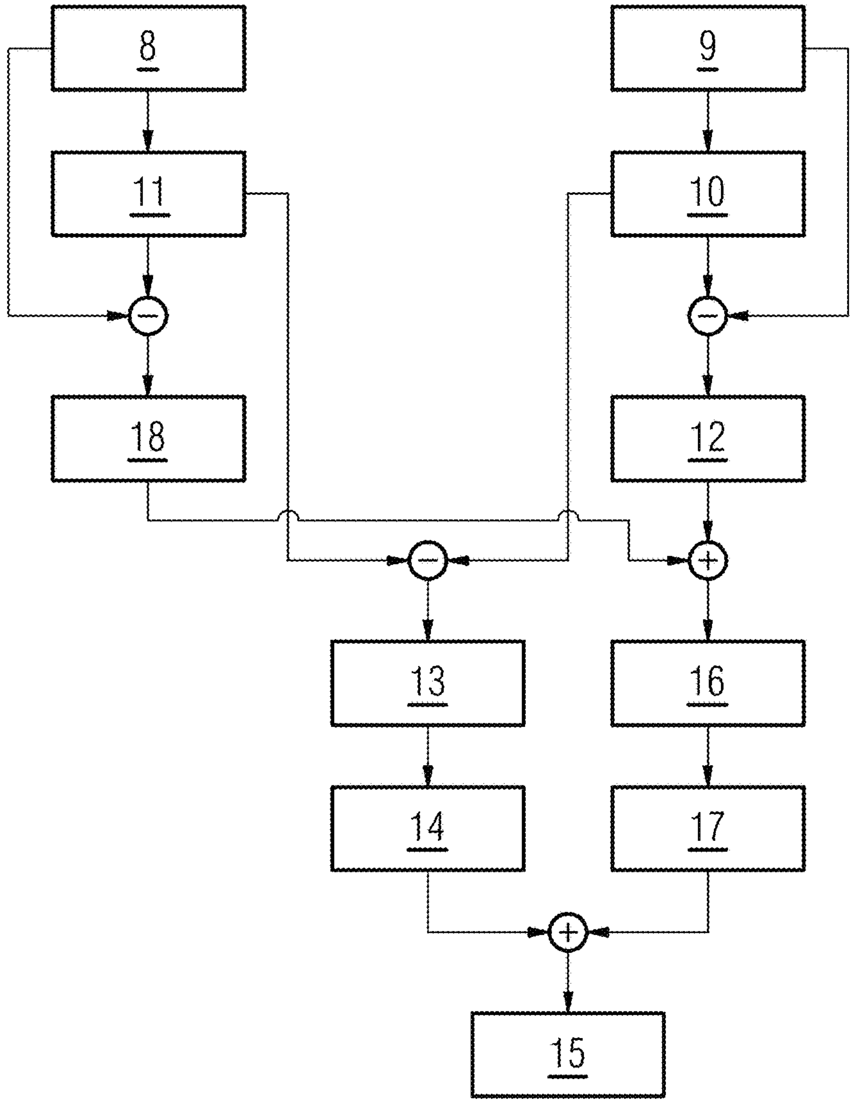
FIG. 4 depicts a schematic flow diagram of a further embodiment of a method for X-ray imaging.

FIG. 4 shows a schematic flow diagram of a further embodiment of a method for X-ray imaging, which is based on the embodiment described in respect of FIG. 2.

Instead of the noise image 19, a noise image 17 is here added to the scaled signal image 14, which depends on the input mask image 8 and the input image 9. By calculating the difference between the input mask image 8 and the mask signal image 11, a mask noise image 18 is generated. The initial noise image 12 is generated by calculating the difference between the input image 9 and the signal image 10. An image 16 dependent on the initial noise image 12 and the mask noise image 18 is generated by addition or weighted addition of the initial noise image 12 and the mask noise image 18. The noise image 17 is generated in that the spatial frequency spectrum 6 of the image 16 is expanded so that the maximum spatial noise frequency corresponding to the first image direction is increased.

In certain embodiments, the input mask image 8 is generated in that on the basis of the first detector data a first raw image is generated, and a variance-stabilizing transformation is applied to the first raw image. A corresponding inverse variance-stabilizing transformation may then be applied to the mask signal image 11 before generating the subtraction image 13. In some embodiments, the input image 9 is generated in that on the basis of the second detector data a second raw image is generated, and a variance-stabilizing transformation is applied to the second raw image. A corresponding inverse variance-stabilizing transformation may then be applied to the signal image 10 before generating the subtraction image 13.

In certain embodiments, one or more grayscale transformations are performed on the mask signal image 11, for example, on the basis of one or more look-up tables, and/or filters for contrast processing are applied before the subtraction image 13 is generated. In certain embodiments, one or more grayscale transformations are performed on the signal image 10, for example, on the basis of one or more look-up tables, and/or filters for contrast processing are applied before the subtraction image 13 is generated.

Figure 5:
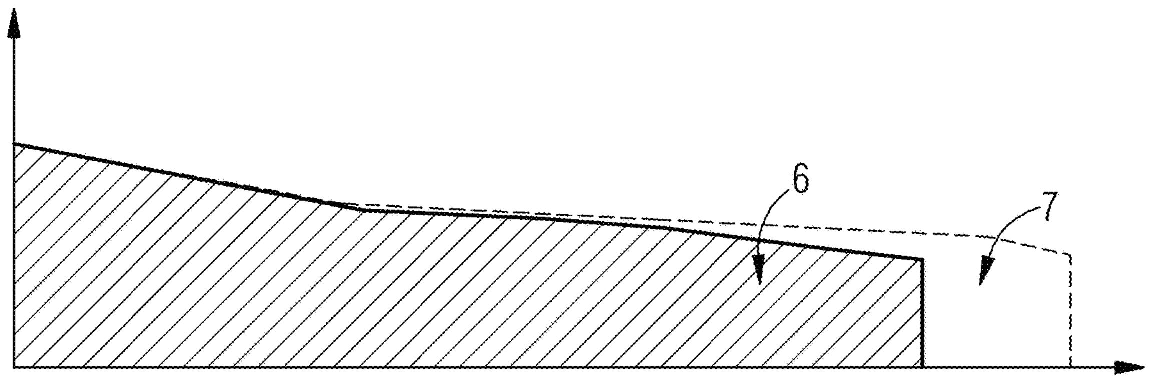
FIG. 5 depicts a schematic representation of a spatial frequency spectrum of an initial noise image or of a noise image corresponding to a further embodiment of a method for X-ray imaging.

FIG. 5 shows, for an exemplary possibility for supplementing the frequency spectrum, a corresponding frequency spectrum 6 of the initial noise image 12 along the first image direction. Due to the discreteness of the initial noise image 12, the frequency spectrum 6 has a maximum spatial noise frequency which limits the frequency space.

To expand or supplement the frequency spectrum, the initial noise image 12 may be scaled in accordance with the subtraction image 13, so that in the first image direction the number of pixels of the scaled initial noise image corresponds to the number of pixels of the scaled subtraction image 14. The scaled initial noise image may then be transformed into the frequency space by applying a discrete two-dimensional FFT.

The still unscaled initial noise image 12 may likewise be transformed into the frequency space. The amplitudes of the resulting frequency spectra of the initial noise image 12 and of the scaled initial noise image may be used to determine a modulation transfer function, MTF, in accordance with the equation:

$$MTF\ (f1, f2) = 1 - \frac{A'(f1, f2)}{A(f1, f2)},$$

where A (f1,f2) represents the corresponding amplitude in the frequency space prior to scaling and A' (f1,f2) represents the corresponding amplitude in the frequency space after scaling.

The MTF may be convoluted with an artificial noise image, for example, an artificial noise image that represents two-dimensional white noise. The result of the convolution corresponds to additional frequency components 7, which may then be added to the frequency spectrum 6 of the scaled initial noise image. The result may then be transformed back into the spatial domain by inverse FFT, in order thus to obtain the noise image 17.

In alternative embodiments, the initial noise image 12 may be split into sub-images corresponding to different frequency bands, for example, by applying the method of Gaussian-Laplacian pyramids or the multiscale analysis of the wavelet theory. The variances of the noise in the individual sub-images may then be determined and artificial noise with the same variance in each case but an increased specified resolution may be inserted into the individual sub-images. The noise image 17 may then be reconstructed by combining the supplemented sub-images. In this way, the performance of the FFT may be avoided, thus reducing the computational effort.

For individual applications or application situations that may arise in the method and that are not explicitly described herein, it may be provided that, according to the method, an error message and/or a request to input user feedback is output and/or a default setting and/or a predetermined initial state is set.

As described, in particular with reference to the figures, disadvantages resulting from the upscaling of the subtraction image may be at least partially overcome by the disclosure.

This is enabled in various embodiments in particular by the separate processing of the noise and signal component. The signal component is processed with an interpolation, for example an edge-adaptive interpolation, while the noise component of the image is changed so that it contains higher noise frequencies than the original image. In certain examples, the noise component may be changed as if the pixel size had not changed during scaling.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for X-ray imaging, the method comprising:
receiving first detector data from an X-ray flat panel detector;
generating an input mask image using the first detector data, wherein the input mask image shows a region to be mapped of an object in a first state;
receiving second detector data from the X-ray flat panel detector;
generating an input image using the second detector data, wherein the input image shows the region to be mapped of the object in a second state;
generating a mask signal image by applying noise suppression to the input mask image;
generating a signal image by applying noise suppression to the input image;
generating an initial noise image by calculating a difference between the input image and the signal image;
generating a subtraction image by calculating a difference between the signal image or an image dependent on the signal image and the mask signal image or an image dependent on the mask signal image;
generating a scaled subtraction image by applying an interpolation method such that, at least in a first image direction, a number of pixels of the scaled subtraction image is greater than a number of pixels of the subtraction image;
generating a noise image, wherein a spatial frequency spectrum of the initial noise image or of an image dependent on the initial noise image is expanded such that a maximum spatial noise frequency corresponding to the first image direction is increased; and
generating a results image in which the scaled subtraction image and the noise image are added together.

2. The method of claim 1, further comprising:
generating a mask noise image by calculating a difference between the input mask image and the mask signal image; and
generating the image dependent on the initial noise image by addition or weighted addition of the initial noise image and the mask noise image,
wherein the noise image is generated such that the spatial frequency spectrum of the image dependent on the initial noise image is expanded, so that the maximum spatial noise frequency corresponding to the first image direction is increased.

3. The method of claim 1, further comprising:
displaying the results image or an image dependent on the results image on a display screen.

4. The method of claim 3, wherein the number of pixels of the scaled subtraction image in the first image direction corresponds to a number of pixels of the display screen in the first image direction.

5. The method of claim 1, wherein the subtraction image is scaled by applying the interpolation method such that a number of pixels of the scaled subtraction image is greater than a number of pixels of the subtraction image in a second image direction.

6. The method of claim 1, further comprising:
emitting, by an X-ray source, X-ray radiation in a direction of the region to be mapped of the object, while the object is in the first state;
generating the first detector data by the X-ray flat panel detector using portions of the X-ray radiation passing through the region to be mapped of the object;
emitting, by the X-ray source, further X-ray radiation in the direction of the region to be mapped of the object, while the object is in the second state; and
generating the second detector data by the X-ray flat panel detector using portions of the further X-ray radiation passing through the region to be mapped of the object.

7. A method for X-ray imaging, the method comprising:
receiving first detector data from an X-ray flat panel detector;
generating an input mask image using the first detector data, wherein the input mask image shows a region to be mapped of an object in a first state;
receiving second detector data from the X-ray flat panel detector;
generating a raw image using the second detector data;
generating an input image using the second detector data, wherein the input image shows the region to be mapped of the object in a second state, and wherein the input image is generated by applying a variance-stabilizing transformation to the raw image;
generating a mask signal image by applying noise suppression to the input mask image;
generating a signal image by applying noise suppression to the input image;
generating a subtraction image by calculating a difference between the signal image or an image dependent on the signal image and the mask signal image or an image dependent on the mask signal image;
generating a scaled subtraction image by applying an interpolation method such that, at least in a first image direction, a number of pixels of the scaled subtraction image is greater than a number of pixels of the subtraction image; and
generating a results image in which the scaled subtraction image and a noise image are added together.

8. The method of claim 7, wherein the variance-stabilizing transformation comprises an Anscombe transformation.

9. The method of claim 7, wherein the image dependent on the signal image is generated such that at least one image processing act is performed, and wherein the at least one image processing act comprises an inverse variance-stabilizing transformation, and/or
wherein the image dependent on the mask signal image is generated such that at least one further image processing act is performed, and wherein the at least one further image processing step comprises a further inverse variance-stabilizing transformation.

10. The method of claim 9, wherein the at least one image processing act comprises at least one grayscale transformation and/or an application of at least one frequency filter, and/or
wherein the at least one further image processing act comprises at least one further grayscale transformation and/or an application of at least one further frequency filter.

11. The method as claimed in claim 10, wherein the at least one grayscale transformation comprises a logarithmic grayscale transformation, and/or
wherein the at least one further grayscale transformation includes a further logarithmic grayscale transformation.

12. The method of claim 7, further comprising:
displaying the results image or an image dependent on the results image on a display screen.

13. The method of claim 12, wherein the number of pixels of the scaled subtraction image in the first image direction corresponds to a number of pixels of the display screen in the first image direction.

14. The method of claim 7, wherein the subtraction image is scaled by applying the interpolation method such that a number of pixels of the scaled subtraction image is greater than a number of pixels of the subtraction image in a second image direction.

15. The method of claim 7, further comprising:

emitting, by an X-ray source, X-ray radiation in a direction of the region to be mapped of the object, while the object is in the first state;

generating the first detector data by the X-ray flat panel detector using portions of the X-ray radiation passing through the region to be mapped of the object;

emitting, by the X-ray source, further X-ray radiation in the direction of the region to be mapped of the object, while the object is in the second state; and generating the second detector data by the X-ray flat panel detector using portions of the further X-ray radiation passing through the region to be mapped of the object.

16. A data processing device comprising:

at least one processor configured to:

receive first detector data from an X-ray flat panel detector;

generate an input mask image using the first detector data, wherein the input mask image shows a region to be mapped of an object in a first state;

receive second detector data from the X-ray flat panel detector;

generate an input image using the second detector data, wherein the input image shows the region to be mapped of the object in a second state;

generate a mask signal image by applying noise suppression to the input mask image;

generate a signal image by applying noise suppression to the input image;

generate an initial noise image by calculating a difference between the input image and the signal image;

generate a subtraction image by calculating a difference between the signal image or an image dependent on the signal image and the mask signal image or an image dependent on the mask signal image;

generate a scaled subtraction image by applying an interpolation method such that, at least in a first image direction, a number of pixels of the scaled subtraction image is greater than a number of pixels of the subtraction image;

generate a noise image, wherein a spatial frequency spectrum of the initial noise image or of an image dependent on the initial noise image is expanded such that a maximum spatial noise frequency corresponding to the first image direction is increased; and generate a results image in which the scaled subtraction image and the noise image are added together.

17. The data processing device of claim 16, wherein the at least one processor is further configured to:

actuate an X-ray source to emit X-ray radiation in a direction of the region to be mapped of the object, while the object is in the first state;

generate the first detector data by the X-ray flat panel detector using portions of the X-ray radiation passing through the region to be mapped of the object;

actuate the X-ray source to emit further X-ray radiation in the direction of the region to be mapped of the object, while the object is in the second state; and generate the second detector data by the X-ray flat panel detector using portions of the further X-ray radiation passing through the region to be mapped of the object.

18. An X-ray imaging system comprising:

an X-ray source;

an X-ray flat panel detector; and a data processing device having at least processor configured to:

actuate the X-ray source to emit X-ray radiation in a direction of a region to be mapped of an object, while the object is in a first state;

actuate the X-ray source to emit further X-ray radiation in the direction of the region to be mapped of the object, while the object is in a second state;

receive first detector data from the X-ray flat panel detector from portions of the X-ray radiation passing through the region to be mapped of the object;

generate an input mask image using the first detector data, wherein the input mask image shows the region to be mapped of the object in the first state;

receive second detector data from the X-ray flat panel detector from portions of the X-ray radiation passing through the region to be mapped of the object;

generate an input image using the second detector data, wherein the input image shows the region to be mapped of the object in the second state;

generate a mask signal image by applying noise suppression to the input mask image;

generate a signal image by applying noise suppression to the input image;

generate an initial noise image by calculating a difference between the input image and the signal image;

generate a subtraction image by calculating a difference between the signal image or an image dependent on the signal image and the mask signal image or an image dependent on the mask signal image;

generate a scaled subtraction image by applying an interpolation method such that, at least in a first image direction, a number of pixels of the scaled subtraction image is greater than a number of pixels of the subtraction image;

generate a noise image, wherein a spatial frequency spectrum of the initial noise image or of an image dependent on the initial noise image is expanded such that a maximum spatial noise frequency corresponding to the first image direction is increased; and generate a results image in which the scaled subtraction image and the noise image are added together.

* * * * *